(12) United States Patent
Nishimura et al.

(10) Patent No.: US 9,415,096 B2
(45) Date of Patent: Aug. 16, 2016

(54) FOXM1 PEPTIDE AND MEDICINAL AGENT COMPRISING THE SAME

(71) Applicant: ONCOTHERAPY SCIENCE, INC., Kanagawa (JP)

(72) Inventors: Yasuharu Nishimura, Kumamoto (JP); Kazunori Yokomine, Kumamoto (JP); Takuya Tsunoda, Kanagawa (JP); Yusuke Nakamura, Tokyo (JP)

(73) Assignee: OncoTherapy Sciences, Inc., Kanagawa (JP)

( * ) Notice: Subject to any disclaimer, the term of this patent is extended or adjusted under 35 U.S.C. 154(b) by 0 days.

(21) Appl. No.: 14/729,752

(22) Filed: Jun. 3, 2015

(65) Prior Publication Data

US 2015/0265689 A1    Sep. 24, 2015

Related U.S. Application Data

(62) Division of application No. 14/036,879, filed on Sep. 25, 2013, now Pat. No. 9,073,968, which is a division of application No. 12/673,432, filed as application No. PCT/JP2008/064437 on Aug. 12, 2008, now Pat. No. 8,569,244.

(30) Foreign Application Priority Data

Aug. 20, 2007   (JP) ................. 2007-214001

(51) Int. Cl.
| | | |
|---|---|---|
| *A61K 38/00* | (2006.01) | |
| *A61K 39/00* | (2006.01) | |
| *C12N 5/0783* | (2010.01) | |
| *C07K 7/08* | (2006.01) | |
| *C07K 7/06* | (2006.01) | |

(52) U.S. Cl.
CPC ............ *A61K 39/0011* (2013.01); *C07K 7/06* (2013.01); *C07K 7/08* (2013.01); *C12N 5/0636* (2013.01); *C12N 5/0638* (2013.01); *A61K 38/00* (2013.01); *A61K 2039/57* (2013.01); *A61K 2039/572* (2013.01); *A61K 2039/585* (2013.01); *C12N 2501/998* (2013.01); *C12N 2502/11* (2013.01)

(58) Field of Classification Search
None
See application file for complete search history.

(56) References Cited

U.S. PATENT DOCUMENTS

| | | | |
|---|---|---|---|
| 5,861,278 | A | 1/1999 | Wong et al. |
| 6,747,137 | B1 | 6/2004 | Weinstock et al. |
| 7,531,300 | B2 | 5/2009 | Nakamura et al. |
| 7,700,573 | B2 | 4/2010 | Nakamura et al. |
| 2005/0260639 | A1 | 11/2005 | Nakamura et al. |
| 2006/0014686 | A1 | 1/2006 | Wonsey et al. |
| 2006/0024692 | A1 | 2/2006 | Nakamura et al. |
| 2006/0216301 | A1 | 9/2006 | Tahara et al. |
| 2007/0083334 | A1 | 4/2007 | Mintz et al. |
| 2009/0162361 | A1 | 6/2009 | Nakamura et al. |
| 2009/0175844 | A1 | 7/2009 | Nakamura et al. |
| 2009/0208514 | A1 | 8/2009 | Nakamura et al. |
| 2009/0286856 | A1 | 11/2009 | Nakamura et al. |
| 2009/0311685 | A1 | 12/2009 | Nakamura et al. |
| 2009/0317392 | A1 | 12/2009 | Nakamura et al. |
| 2010/0173317 | A1 | 7/2010 | Nakamura et al. |
| 2011/0152199 | A1 | 6/2011 | Nishimura et al. |
| 2012/0014996 | A1 | 1/2012 | Nakamura et al. |

FOREIGN PATENT DOCUMENTS

| | | |
|---|---|---|
| CA | 2 696 597 A1 | 2/2009 |
| EP | 846761 A1 | 6/1998 |
| EP | 1462456 A1 | 9/2004 |
| EP | 1806413 A1 | 7/2007 |
| EP | 2189471 A1 | 5/2010 |
| JP | 11-510507 A | 9/1999 |
| JP | 2005-518192 A | 6/2005 |
| JP | 2006-141208 A | 6/2006 |
| JP | 2007-530006 A | 11/2007 |
| TW | 2006/00785 A | 1/2006 |
| WO | 97/05900 A1 | 2/1997 |
| WO | 02/099076 A2 | 12/2002 |
| WO | 03/037060 A2 | 5/2003 |
| WO | 03/050140 A1 | 6/2003 |

(Continued)

OTHER PUBLICATIONS

Burgess et al., "Possible Dissociation of the Heparing-binding and Mitogenic Activities of Heparin-binding (Acidic Fibroblast) Growth Factor-1 from its Receptor-binding Activiteis by Site-directed Mutagenesis of a Single Lysine Residue" *Journal of Cell Biology*, vol. 111, pp. 2129-2138 (1990).

(Continued)

*Primary Examiner* — Sheela J Huff
(74) *Attorney, Agent, or Firm* — Kilpatrick Townsend & Stockton LLP (57) ABSTRACT

An objective of the present invention is to provide a means for enabling cancer immunotherapy that targets approximately 30% of various cancer patients that highly express forkhead box M1 (FOXM1) among the Japanese, by identifying FOXM1-derived peptides that can activate cancer cell-damaging human killer T cells by binding to HLA-A2. The present invention provides a peptide of (A) or (B) below:

(A) a peptide including the amino acid sequence of any one of SEQ ID NOs: 1 to 3;

(B) a peptide which includes the amino acid sequence of any one of SEQ ID NOs: 1 to 3, wherein one, two, or several amino acid(s) are substituted, deleted, inserted, and/or added, and wherein the peptide shows cytotoxic (killer) T cell-inducing activity.

2 Claims, 1 Drawing Sheet

(56) References Cited

FOREIGN PATENT DOCUMENTS

| WO | 2004/019761 A2 | 3/2004 |
| --- | --- | --- |
| WO | 2004/024766 A1 | 3/2004 |
| WO | 2004/031412 A2 | 4/2004 |
| WO | 2004/031413 A2 | 4/2004 |
| WO | 2004/100977 A1 | 11/2004 |
| WO | 2005/028676 A2 | 3/2005 |
| WO | 2005/058937 A2 | 6/2005 |
| WO | 2005/090603 A2 | 9/2005 |
| WO | 2005/090991 A1 | 9/2005 |
| WO | 2006/085684 A2 | 8/2006 |
| WO | 2007/013665 A2 | 2/2007 |
| WO | 2007/013671 A2 | 2/2007 |
| WO | 2007/123247 A1 | 11/2007 |
| WO | 2009/025117 A1 | 2/2009 |
| WO | 2010/095428 A1 | 8/2010 |

OTHER PUBLICATIONS

Guo, et al., "Different length peptides bind to HLA-Aw68 similarly at their ends but bulge out in the middle", *Nature*, vol. 360, p. 364-366 (1992).

Lazar et al.,"Transforming growth factor alpha: mutation of aspartic acid 47 and leucine 48 results in different biological activities", *Molecular and Cellular Biology*, vol. 8, No. 3, pp. 1247-1252 (1988).

Abelev, "Immunology of Human Tumors," (2000) *Nature*, vol. 2, pp. 20-25.

Adams, et al., "Prediction of binding to MHC class I molecules," *J Immunol Methods*, vol. 185(2), pp. 181-190 (Sep. 25, 1995).

Andre, et al., "Exosomes as Potent Cell-Free Peptide-Based Vaccine. I. Dendritic Cell-Derived Exosomes Transfer Functional MHC Class I/Peptide Complexes to Dendritic Cells," *J Immunol.*, vol. 172(4), pp. 2126-2136 (Feb. 15, 2004)

Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al, "Human Tumor Antigens Recognized by T Lymphocytes," *J Exp Med.*, vol. 183(3), pp. 725-729 (Mar. 1, 1996).

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).

Coulie,et al., "Cytolytic T-cell responses of cancer patients vaccinated with a MAGE antigen," *Immunol Rev.*, vol. 188, pp. 33-42 (Oct. 2002).

Dermer, *Bio/Technology*, vol. 12, p. 320 (1994).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314(Apr. 2004, Epub Nov. 5, 2003).

Engelhard, *Current Opinion in Immunology*, vol. 6, p. 13 (1994).

Ezzell, *J. NIH Res.*, vol. 7, p. 46 (1995).

Falk, et al., "Allele-specific motifs revealed by sequencing of self-peptides eluted from MHC molecules," *Nature*, vol. 351(6324), pp. 290-296 (May 23, 1991).

Freshney, Culture of Animal Cells, A Manual of Basic Technique, Alan R. Liss, New York, p. 4 (1983).

Fujie, et al., "A MAGE-1-Encoded HLA-A24-Binding Synthetic Peptide induces Specific Anti-Tumor Cytotoxic T Lymphocytes," *Int J Cancer*, vol. 80(2), pp. 169-172 (Jan. 18, 1999).

Guidance for Industry, Clinical Considerations for Therapeutic Cancer Vaccines, 18 pages (Oct. 2011).

Guo, et al., *Nature*, vol. 360, p. 384 (1992).

Gura, *Science*, vol. 278, pp. 1041-1042 (1997).

Gusarova, et al., "A cell-penetrating ARF peptide inhibitor of FoxM1 in mouse hepatocellular carcinoma treatment," *J Clin Invest.*, vol. 117(1), pp. 99-111 (Jan. 2007, Epub Dec. 14, 2006).

Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).

Hoffman, et al., "The Abilitiy of Variant Peptides to Reverse the Nonresponsiveness of T Lymphocytes to the Wild-Type Sequence p53264-272 Epitope," *J Immunol*, vol. 168(3), pp. 1338-1347 (Feb. 1, 2002).

Ishizaki, et al., "Inhibition of Tumor Growth with Antiangiogenic Cancer Vaccine Using Epitope Peptides Derived from Human Vascular Endothelial Growth Factor Receptor," *Clin Cancer Res.*, vol. 12(19), pp. 5841-5849 (Oct. 1, 2006).

Jain, *Sci. Am.*, vol. 271, pp. 58-65 (1994).

Johnson, et al., *Cancer Treatment Reviews*, vol. 2, p. 1 (1975).

Kalinichenko, et al., "Foxm1b transcription factor is essential for development of hepatocellular carcinomas and is negatively regulated by the p19ARF tumor suppressor," *Genes Dev.*, vol. 18(7), pp. 830-850 (Apr. 1, 2004).

Kikuchi,et al., "Identification of a Sart-1-Derived Peptide Capable of Inducing HLA-A-A24-Restricted and Tumor-Specific Cytotoxic T Lymphocytes," *Int J Cancer*, vol. 81(3), pp. 459-466 (May 5, 1999).

Kim, et al., "The Forkhead Box m1 Transcription Factor Stimulates the Proliferation of Tumor Cells during Development of Lung Cancer," *Cancer Res.*, vol. 66(4), pp. 2153-2161 (Feb. 15, 2006).

Komori, et al., "Identification of HLA-A2- or HLA-A24-Restricted CTL Epitopes Possibly Useful for Glypican-3-Specific Immunotherapy of Hepatocellular Carcinoma," *Clin Cancer Res.*, vol. 12(9), pp. 2689-2697 (May 1, 2006).

Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).

Kubo, et al., "Definition of Specific Peptides Motifs for Four Major HLA-A Alleles," *J Immunol.*, vol. 152(8), pp. 3913-3924 (Apr. 15, 1994).

Laoukili, et al., "FoxM1 is required for execution of the mitotic programme and chromosome stability," *Nat Cell Biol.*, vol. 7(2), pp. 126-136 (Feb. 2005, Epub Jan. 16, 2005)

Laoukili, et al., "FoxM1: At the crossroads of ageing and cancer," *Biochim Biophys Acta.*, vol. 1775(1), pp. 92-102 (Jan. 2007, Aug. 30, 2006).

Lee, et al., "Increased Vaccine-Specific T Cell Frequency After Peptide-Based Vaccination Correlates with Increased Stimulation to In Vitro Stimulation But Does Not Lead to Tumor Regression," *J Immunol.*, vol. 163(11), pp. 6292-6300 (Dec. 1, 1999).

NCI Cancer Bulletin, vol. 5(10), 8-9, 11 pages (May 13, 2008).

Obama, et al., "Genome-Wide Analysis of Gene Expression in Human Intrahepatic Cholangiocarcinoma," *Hepatology*, vol. 41(6), pp. 1339-1348 (Jun. 2005).

Oiso, et al., "A Newly Identified MAGE-3-Derived Epitope Recognized by HLA-A24-Restricted Cytotoxic T Lymphocytes," *Int J Cancer*, vol. 81(3), pp. 387-394 (May 5, 1999).

Parker, et al., "Scheme for Ranking Potential HLA-A2 Binding Peptides Based on Independent Binding of Individual peptide Side-Chains," *J Immunol.*, vol. 152(1), pp. 163-175 (Jan. 1, 1994).

Radhakrishnan, et al., "Identification of a Chemical Inhibitor of the Oncogenic Transcription Factor Forkhead Box M1," *Cancer Res.*, vol. 66(19), pp. 9731-9735 (Oct. 1, 2006).

Rammensee, et al., "MHC ligands and peptide motifs: first listing," *Immunogenetics*, vol. 41(4), pp. 178-228 (1995).

Roitt, et al., *Immunology*, M:Mir; pp. 159, 162-163, 195-196,196-199 (2000).

Roitt, et al., *Immunology*, translation from English, M: MIR: pp. 160-163 (2000).

Rosenberg, et al., "Cancer immunotherapy: moving beyond current vaccines," *Nat Med.*, vol. 10(9), pp. 909-915 (Sep. 2004).

Schueler-Furman, et al., "Structure-based prediction of binding to MHC class I molecules: Application to a broad range of alleles," *Protein Sci.*, vol. 9(9), pp. 1838-1846 (Sep. 2000).

Schwartzentruber, et al., "gp100 Peptide Vaccine and Interleukin-2 in Patients with Advanced Melanoma," *N Engl J Med.*, vol. 364(22), pp. 2119-2127 (Jun. 2, 2011)

(56) References Cited

OTHER PUBLICATIONS

Shastri, et al., *J. Immunol.* vol. 155, p. 4339 (1995).
Spitler, *Cancer Biotheraphy*, vol. 10, pp. 1-3 (1995).
Takahashi, et al., "The Neuromedin U-Growth Hormone Secretagogue Receptor 1b/Neuorotensin Receptor 1 Oncogenic Signaling Pathway as a Therapeutic for Lung Cancer," *Cancer Res.*, vol. 66(19), pp. 9408-9419 (Oct. 1, 2006).
Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).
U.S. Appl. No. 13/536,327, 204 pages, filed Jun. 28, 2012.
U.S. Appl. No. 13/113,732, filed May 23, 2011, 172 pgs.
U.S. Appl. No. 13/202,078, which is a U.S. National Stage of PCT/JP2010/001005, filed Feb. 17, 2010, 50 pages.
U.S. Appl. No. 13/238,273, filed Sep. 21, 2011, 120 pages.
U.S. Appl. No. 13/246,639, filed Sep. 27, 2011, 164 pages.
Van Der Burg, et al., "Immunogenicity of Peptides Bound to MHC Class 1 Molecules Depends on the MHC-Peptide Complex Stability," *J Immunol.*, vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).
Wang, et al., "The Forkhead Box m1b transcription factor is essential for hepatocyte DNA replication and mitosis during mouse liver regeneration," *Proc Natl Acad Sci USA*, vol. 99(26), pp. 16881-16886 (Dec. 24, 2002, Epub Dec. 13, 2002).
Wonsey, et al., "Loss of the Forkhead Transcription Factor FoxM1 Causes Centrosome Amplification and Mitotic Catastrophe," *Cancer Res.*, vol. 65(12), pp. 5181-5189 (Jun. 15, 2005).
Yokomine, et al., "FOXM1, a novel cancer-associated antigen useful for immunotherapy of cholangiocarcinoma and lung cancer," Abstract of the 66th Annual Meeting of the Japanese Cancer Association, pp. 164(#P-295) (2007).
Yokomine, et al., "The forkhead box M1 transcription factor as a candidate of target for anti-cancer immunotherapy," *Int J Cancer*, vol. 126(9), pp. 2153-2163 (May 1, 2010)
Yoshida, et al., "The Forkhead Box M1 Transcription Factor Contributes to the Development and Growth of Mouse Colorectal Cancer," *Gastroenterology*, vol. 132(4), pp. 1420-1431 (Apr. 2007, EPub Jan. 25, 2007).
Zaremba, et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).
Luscher-Firzlaff et al., "Interaction of the fork head domain transcription factor MPP2 with the human papilloma virus 16 E7 proein: enhancement of transformation and transactivation", *Oncogene*, vol. 18, pp. 5620-5630 (1999).
Marsh et al., *The HLA FactsBook*, San Diego: Academic Press, pp. 121 (2000).
NCBI GenBank Accession No. NM_202002.1, "*Homo sapiens* forkhead box Ma (FOXM1), transcript variant 1, mRNA", Nov. 13, 2006.
Blohm et al., "Lack of Effector Cell Function and Altered Tetramer Binding of Tumor-Infiltrating Lymphocytes", J Immunol., vol. 169, No. 10, pp. 5522-5530 (2002).
Prevost-Blondel et al., "Tumor-Infiltrating Lymphocytes Exhibiting High Ex Vivo Cytolytic Activity Fail to Prevent Murine Melanoma Tumor Growth in Vivo", J Immunol, vol. 161, No. 5, pp. 2187-2194 (1998).
Roitt et al., Immunology, 2000, pp. 162-164.
Corresponding English document of Roitt et al., Immunology, 2000, pp. 162-164 (p. 114-118).
Tan et al., "Rapid Death of Adoptively Transferred T Cells in Acquired Immunodeficiency Syndrome", Blood, vol. 93, No. 5, pp. 15066-1510 (1999).
White et al., "Production and Characterization of T Cell Hybridomas", T Cell Protocols. Humana Press, pp. 185-193 (2000).

Fig. 1A
ELISPOT ASSAY

Fig. 1B
CYTOTOXICITY TEST

US 9,415,096 B2

SEQUENCE LISTING

<160> NUMBER OF SEQ ID NOS: 23

<210> SEQ ID NO 1
<211> LENGTH: 9
<212> TYPE: PRT
<213> ORGANISM: Artificial
<220> FEATURE:
<223> OTHER INFORMATION: peptide vaccine

<400> SEQUENCE: 1

Tyr Leu Val Pro Ile Gln Phe Pro Val
1               5

<210> SEQ ID NO 2
<211> LENGTH: 10
<212> TYPE: PRT
<213> ORGANISM: Artificial
<220> FEATURE:
<223> OTHER INFORMATION: peptide vaccine

<400> SEQUENCE: 2

Ser Leu Val Leu Gln Pro Ser Val Lys Val
1               5                   10

<210> SEQ ID NO 3
<211> LENGTH: 10
<212> TYPE: PRT
<213> ORGANISM: Artificial
<220> FEATURE:
<223> OTHER INFORMATION: peptide vaccine

<400> SEQUENCE: 3

Gly Leu Met Asp Leu Ser Thr Thr Pro Leu
1               5                   10

<210> SEQ ID NO 4
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 4

Asn Gln Ala Glu Ala Ser Lys Glu Val
1               5

<210> SEQ ID NO 5
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 5

Tyr Met Ala Met Ile Gln Phe Ala Ile
1               5

<210> SEQ ID NO 6
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 6

Arg Met Thr Leu Lys Asp Ile Tyr Thr
1               5

```
<210> SEQ ID NO 7
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 7

Asn Leu Ser Leu His Asp Met Phe Val
1               5

<210> SEQ ID NO 8
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 8

Ser Leu His Asp Met Phe Val Arg Glu Thr
1               5                   10

<210> SEQ ID NO 9
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 9

Leu Leu Pro Arg Val Ser Ser Tyr Leu
1               5

<210> SEQ ID NO 10
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 10

Leu Leu Pro Arg Val Ser Ser Tyr Leu Val
1               5                   10

<210> SEQ ID NO 11
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 11

Ile Gln Phe Pro Val Asn Gln Ser Leu Val
1               5                   10

<210> SEQ ID NO 12
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 12

Leu Val Leu Gln Pro Ser Val Lys Val
1               5
```

```
<210> SEQ ID NO 13
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 13

Leu Leu Ala Glu Glu Gly Ile Ala Pro Leu
1               5                   10

<210> SEQ ID NO 14
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 14

Leu Leu Phe Gly Glu Gly Phe Ser Pro Leu
1               5                   10

<210> SEQ ID NO 15
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 15

Leu Leu Phe Ser Glu Gly Pro Ser Thr
1               5

<210> SEQ ID NO 16
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 16

Ser Gln Leu Ser Tyr Ser Gln Glu Val
1               5

<210> SEQ ID NO 17
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 17

Lys Val Gly Gly Ile Asp Phe Ser Pro Val
1               5                   10

<210> SEQ ID NO 18
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 18

Arg Leu Leu Ser Ser Glu Pro Leu Asp Leu
1               5                   10
```

```
<210> SEQ ID NO 19
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 19

Leu Leu Ser Ser Glu Pro Leu Asp Leu
1               5

<210> SEQ ID NO 20
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 20

Ser Leu Thr Glu Gly Leu Val Leu Asp Thr
1               5                   10

<210> SEQ ID NO 21
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 21

Thr Met Asn Asp Ser Leu Ser Lys Ile
1               5

<210> SEQ ID NO 22
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 22

Ile Leu Leu Asp Ile Ser Phe Pro Gly Leu
1               5                   10

<210> SEQ ID NO 23
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 23

Leu Leu Asp Ile Ser Phe Pro Gly Leu
1               5
```

FOXM1 PEPTIDE AND MEDICINAL AGENT COMPRISING THE SAME

CROSS-REFERENCES TO RELATED APPLICATIONS

The present application is a divisional of U.S. application Ser. No. 14/036,879, filed Sep. 25, 2013, which is a divisional of Ser. No. 12/673,432, filed Mar. 7, 2011, now U.S. Pat. No. 8,569,244, which is a U.S. National Phase of PCT/JP2008/064437, filed Aug. 12, 2008, which claims the benefit of Japanese Application No. 2007-214001, filed on Aug. 20, 2007, the disclosures of which are hereby incorporated herein by reference in their entirety.

REFERENCE TO SEQUENCE LISTING

This application includes a Sequence Listing as a text file named 87331-946183_SEQ_LIST.txt" created May 29, 2015, and containing 5,225 bytes. The material contained in this text file is incorporated by reference in its entirety for all purposes.

TECHNICAL FIELD

The present invention relates to novel peptides that are useful as vaccines against cancers highly expressing forkhead box M1 (FOXM1), such as biliary tract cancer, lung cancer, and pancreatic cancer, and to pharmaceuticals including the peptides for treatment and prevention of tumors.

BACKGROUND ART

The number of biliary tract cancer (gallbladder cancer and cholangiocarcinoma) deaths is on the rise in Japan, and 16,586 people died of the cancer in 2005. In most biliary tract cancer cases, no subjective symptoms are present in the early stages. Compared to cancers that form on the inside of the digestive tract, such as stomach cancer and colon cancer, accurate visualization and diagnostic imaging of biliary tract cancer is difficult. Therefore, early detection of biliary tract cancer is difficult, and the cancer has often already progressed and is unresectable when it is found. Besides surgical therapy, radiation therapy and chemotherapy are performed for treatment of biliary tract cancer, but they are not therapeutically effective, and thus the establishment of new therapeutic methods is urgently needed.

Lung cancer deaths are also on the rise in Japan, and 62,063 people died of the cancer in 2005. At present, lung cancer accounts for 19.0% of the cancer deaths in Japan, and it has been the leading cause of cancer death since 2000. Smoking is said to be the main cause of the onset of lung cancer. Besides smoking, inhalation of asbestos or radon gas is also believed to cause lung cancer. Smoking cessation is encouraged and health checks are carried out as measures to prevent lung cancer. However, although it is decreasing, the smoking population in Japan in 2005 is still estimated to be approximately 30 million. Furthermore, recently, it has been shown that simple chest X-ray imaging and sputum test widely performed during health checks are not effective for early detection of lung cancer, and thus they do not lead to reduction of cancer deaths. Considering the above, the number of lung cancer deaths is predicted to continue increasing in the future.

The symptoms of lung cancer include cough, bloody sputum, shortness of breath, and chest pain, but in most cases, symptoms are absent in the early stages. When symptoms appear, the cancer has already progressed in many cases. Therefore, more than half of the patients are inoperable when the cancer is first discovered, and it is regarded as one of the intractable cancers. The recovery rate after operation is not as good as other cancers, and the overall five-year survival rate after surgery is just short of 50%. In recent years, the five-year survival rate for early-stage lung cancer is increasing as a result of advances in multimodal treatment by radiotherapy, chemotherapy, and such with surgical resection as the main treatment; however, improvement of the therapeutic effects for advanced lung cancer is poor, and the establishment of new therapeutic strategies is in urgent need.

The number of pancreatic cancer deaths is also on the increase in Japan, and 22,927 people died of the cancer in 2005. At present, pancreatic cancer accounts for 7.0% of the cancer deaths in Japan, and ranks fifth following lung cancer, stomach cancer, colon cancer, and liver cancer. There are no symptoms specific to pancreatic cancer, and in many cases when symptoms appear, the cancer has already progressed. Even today with advances in diagnostic imaging, approximately 40% of total Japanese pancreatic cancer patients belong to advanced cases with distant metastasis, and many patients are found to have unresectable locally-advanced cancer. Therefore, the overall five-year survival rate of the patients is 5% or less, and the prognosis after diagnosis is very poor. Due to the difficulty in diagnosis, the incidence of pancreatic cancer as a cause of cancer death is gradually increasing particularly in advanced countries. Although multimodal treatment by radiotherapy, chemotherapy, and such with surgical resection as the central treatment is presently carried out, there is no dramatic improvement in the therapeutic effects, and the establishment of novel therapeutic strategies is urgently needed. Various factors such as lifestyle habits including smoking, obesity, diet, alcohol drinking, and coffee drinking, as well as chronic pancreatitis, diabetes, genetic factors, and such have been suggested to be involved in causing the onset of pancreatic cancer.

On the other hand, recent development in molecular biology and tumor immunology has elucidated that cytotoxic (killer) T cells and helper T cells recognize peptides generated by degradation of proteins that are specifically and highly expressed in cancer cells and which are presented on the surface of cancer cells or antigen presenting cells via HLA molecules, and cause immunoreaction to destroy cancer cells. Furthermore, many tumor antigen proteins and peptides derived therefrom, which stimulate such immunoreaction to attack cancer, have been identified, and antigen-specific tumor immunotherapy is being clinically applied.

The HLA class I molecule is expressed on the surface of all nucleated cells of the body. It binds to a peptide generated by intracellular degradation of proteins produced in the cytoplasm or nucleus, and expresses the peptide on the cell surface. On the surface of a normal cell, peptides derived from normal autologous proteins bind to HLA class I molecules, and are not recognized and destroyed by T cells of the immune system. On the other hand, in the process of becoming a cancer, cancer cells sometimes express a large quantity of proteins that are hardly or slightly expressed in normal cells. When HLA class I molecules bind to peptides generated by intracellular degradation of proteins specifically and highly expressed in cancer cells, and then express the peptides on the surface of cancer cells, killer T cells recognize and destroy only the cancer cells. By administering such cancer-specific antigens or peptides to an individual, cancer cells can be destroyed and cancer growth can be suppressed without harming normal cells. This is called cancer immunotherapy using cancer-specific antigens. HLA class II molecules are mainly expressed on the surface of antigen-presenting cells. The molecules bind to peptides derived from cancer-specific antigens, which are generated by intracellular degradation of cancer-specific antigens incorporated into antigen-presenting cells from outside of the cells, and then express the peptides on the surface of the cells. Helper T cells that recognize them are activated, and induce or enhance immunoreaction against tumors by producing various cytokines that activate other immunocompetent cells.

Accordingly, if an immunotherapy that targets antigens specifically and highly expressed in cancers is developed, such a therapy can effectively eliminate cancers alone without causing any harmful event on normal autologous organs. It is also expected that the therapy can be used for any terminal cancer patients to whom other treatments cannot be applied. In addition, by administering a cancer-specific antigen and peptide as a vaccine in advance to individuals with a high risk of developing cancers, cancer development can be prevented.

The present inventors first conducted genome-wide gene expression analysis on 27,648 human genes using cDNA microarrays to investigate the expression profiles of these genes in 25 intrahepatic bile duct cancer cases and in various normal organs including those in the embryonic stage. As a result, the present inventors discovered that Forkhead box m1 (FOXM1) (GenBank Accession No. NM_202003) was very highly expressed in the tissues of many intrahepatic bile duct cancer cases. Similar to and in addition to intrahepatic bile duct cancer, FOXM1 was found to be highly expressed in almost all the cases of lung cancer, bladder cancer, and pancreatic cancer. Furthermore, high expression of FOXM1 was found in 40% or more of the cases in a wide variety of cancers such as cervical cancer, ovarian cancer, malignant lymphoma, breast cancer, stomach cancer, esophageal cancer, prostate cancer, hepatocellular carcinoma, colon cancer, and chronic myeloid leukemia. These facts suggest that FOXM1 could serve as a cancer-specific antigen in various cancers. FOXM1 is expressed in embryonic liver, and in normal adult organs, it is slightly expressed in the digestive tract such as stomach, small intestine, and large intestine, thymus, and testis; however, the expression level is remarkably low compared to cancerous parts.

Examples of the documents indicating that FOXM1 is related to the onset of cancer and the regulation of cell proliferation include Non-patent Documents 1 to 10. However, none of the documents describes the use of FOXM1 as a vaccine against cancer.

[Non-patent document 1] Yoshida Y, Wang I-C, Yoder H M, Davidson N O, Costa R H.: The forkhead box M1 transcription factor contributes to the development and growth of mouse colorectal cancer. Gastroenterology 132: 1420-1431, 2007.

[Non-patent document 2] Gusarcova G A, Wang I-C, Major M L, Kalinichenko V V, Ackerson T, Petrovi V, Costa R H.: A cell-penetrating ARF peptide inhibitor of FOXM1 in mouse hepatocellular carcinoma treatment. J. Clin. Invest. 117: 99-111, 2007.

[Non-patent document 3] Radhakrishnan S K, Bhat U G, Hughes D E, Wang I-C, Costa R H, Gartel A L.: Identification of a chemical inhibitor of the oncogenic transcription factor forkhead box M1. Cancer Res. 66: 9731-9735, 2006.

[Non-patent document 4] Takahashi K, Furukawa C, Takano A, Ishikawa N, Kato T, Hamaya S, Suzuki C, Yasui W, Inai K, Sone S, Ito T, Nishimura H, Tsuchiya E, Nakamura Y, Daigo Y.: The neuromedin U-growth hormone secretagogue receptor 1b/neurotensin receptor 1 oncogenic signaling pathway as a therapeutic target for lung cancer. Cancer Res. 66: 9408-9419, 2006.

[Non-patent document 5] Kim I-M, Ackerson T, Ramakrishna S, Tretiakova M, Wang I-C, Kalin T V, Major M L, Gusarova G A, Yoder H M, Costa R H, Kalinichenko V V.: The forkhead box m1 transcription factor stimulates the proliferation of tumor cells during development of lung cancer. Cancer Res. 66: 2153-2161, 2006.

[Non-patent document 6] Wonsey D R, Folletie M.: Loss of the forkhead transcription factor FoxM1 causes centrosome amplification and mitotic catastrophe. Cancer Res. 65: 5181-5189, 2005.

[Non-patent document 7] Obama K, Ura K, Li M, Katagiri T, Tsunoda T, Nomura A, Satoh S, Nakamura Y, Furukawa Y: Genome-wide analysis of gene expression in human intrahepatic cholangiocarcinoma. Hepatology 41: 1339-1348, 2005.

[Non-patent document 8] Laoukili J, Kooistra M R H, Bras A, Kauw J, Kerkhoven R M, Morrison A, Clevers H, Medema R H.: Foxml is required for execution of the mitotic programme and chromosome stability. Nature Cell Biol. 7: 126-136, 2005.

[Non-patent document 9] Kalinichenko V V, Major M, Wang X, Petrovic V, Kuechle J, Yoder H M, Shin B, Datta A, Raychaudhuri P, Costa R H.: Foxmlb transcription factor is essential for development of hepatocellular carcinomas and is negatively regulated by the $p19^{ARF}$ tumor suppressor. Genes Dev. 18: 830-850, 2004.

[Non-patent document 10] Wang X, Kiyokawa H, Dennewitz M B, Costa R H.: The forkhead box m1b transcription factor is essential for hepatocyte DNA replication and mitosis during mouse liver regeneration. Proc. Natl. Acad. Sci. USA 99: 16881-16886, 2002.

DISCLOSURE OF THE INVENTION

[Problems to be Solved by the Invention]

An objective of the present invention is to develop a means for carrying out immunotherapy that suppresses cancer growth by enhancing the anti-cancer immunity of cancer patients as a novel therapeutic method for metastatic or intractable cancers that are difficult to be treated by surgical therapy, chemotherapy, and radiotherapy which are conducted as therapeutic methods for biliary tract cancer, lung cancer, pancreatic cancer, and such. More specifically, an objective of the present invention is to identify peptides that are derived from proteins highly and specifically expressed in cancers and can induce strong immunoreaction against the above-mentioned cancers without causing adverse events in cancer patients, and to apply these peptides in tumor immunotherapy. The present invention enables immunotherapy for approximately 30% of the Japanese patients with the above-mentioned cancers, by identifying peptides that are derived from a protein highly and specifically expressed in the above-mentioned cancers and are presented to killer T cells by HLA-A2.

[Means for Solving the Problems]

Herein, the present inventors induced FOXM1 peptide-specific killer T cells by in vitro stimulation of human CD8 positive killer T cells by co-culturing them with human peripheral blood monocyte-derived dendritic cells pulsed with human FOXM1 peptides which have an HLA-A2 binding motif Whether or not there was induction of killer T cells specific to each FOXM1 peptide was examined by detecting γ-interferon (IFN-γ) produced by the killer T cells activated from recognition of the peptide presented by HLA-A2 using ELISPOT assay. As a result, novel FOXM1 peptides that are potentially candidate target antigens applicable to immunotherapy were identified. Furthermore, it was revealed that FOXM1-responsive CTLs induced using the aforementioned peptides have specific cytotoxicity against cancer cells expressing endogenous FOXM1 and HLA-A2 molecules, and that the CTLs recognize target cells in an HLA class I-restricted manner.

More specifically, the present invention provides the following:

[1] a peptide of (A) or (B) below:
(A) a peptide including the amino acid sequence of any one of SEQ ID NOs: 1 to 3;
(B) a peptide which includes the amino acid sequence of any one of SEQ ID NOs: 1 to 3, wherein one, two, or several amino acid(s) are substituted, deleted, inserted, and/or added, and wherein the peptide shows cytotoxic (killer) T cell-inducing activity;
[2] the peptide of [1], wherein the second amino acid from the N terminus is leucine or methionine;
[3] the peptide of [1], wherein the C-terminal amino acid is valine or leucine;
[4] an agent for inducing immunity against cancer, which includes one or more peptide(s) of [1] as an active ingredient;
[5] an agent for treating and/or preventing cancer, which includes one or more peptide(s) of [1] as an active ingredient;
[6] an agent for inducing an antigen presenting cell that shows cytotoxic (killer) T cell-inducing activity, wherein said agent includes one or more peptide(s) of [1] as an active ingredient;
[7] an agent for inducing an antigen-presenting cell that shows cytotoxic (killer) T cell-inducing activity, wherein said agent includes one or more polynucleotide(s) encoding the peptide of [1] as an active ingredient;
[8] an agent for inducing a cytotoxic (killer) T cell, wherein said agent includes one or more peptide(s) of [1] as an active ingredient;
[9] an antibody against the peptide of [1];
[10] a cytotoxic (killer) T cell, a helper T cell, or an immunocyte population including them, which is induced using the peptide of [1];
[11] an antigen-presenting cell that presents a complex including the peptide of [1] and an HLA antigen;
[12] the antigen-presenting cell of [11], which is induced by the agent of [6] or [7];
[13] an exosome that presents a complex including the peptide of [1] and an HLA antigen;
[14] the exosome of [13], wherein the HLA antigen is HLA-A2 (HLA-A*0201);
[15] a method for inducing an antigen-presenting cell that shows cytotoxic (killer) T cell-inducing activity, which includes the step of contacting an antigen-presenting cell with the peptide of [1];
[16] a method for inducing an antigen-presenting cell that shows cytotoxic (killer) T cell-inducing activity, which includes the step of introducing a polynucleotide encoding the peptide of [1] into an antigen presenting cell;
[17] a method for inducing a cytotoxic (killer) T cell, which includes the step of contacting a T cell with the peptide of [1];

The present invention also provides the following:

[18] a method for inducing immunity against cancer, which includes the step of administering the peptide of [1] to a subject;
[19] a method for treating and/or preventing cancer, which includes the step of administering the peptide of [1] to a subject;
[20] use of the peptide of [1] in the production of an agent for inducing immunity against cancer;
[21] use of the peptide of [1] in the production of an agent for treating and/or preventing cancer;
[22] the peptide of [1], for induction of immunity against cancer;
[23] the peptide of [1], for treatment and/or prevention of cancer.

BRIEF DESCRIPTION OF THE DRAWINGS

FIGS. 1A and 1B show the results of ELISPOT assay and cytotoxicity test. CD8 positive T cells were isolated from the peripheral blood of HLA-A2 positive healthy individuals and breast cancer patients. Killer T cells obtained by stimulation with monocyte-derived dendritic cells pulsed with each FOXM1 peptide were examined by ELISPOT assay to determine whether they react specifically to the FOXM1 peptides and produce IFN-γ. Furthermore, whether or not FOXM1-expressing cells are specifically injured in an HLA-A2 restricted manner was examined by cytotoxicity test. T2-A2 cells were used as the target cells in the ELISPOT assay. T2-A2 cells are a cell line produced by introducing the HLA-A2 gene into a mouse T2 cell line deficient in TAP gene expression. Due to TAP deficiency in T2-A2 cells, a complex formed with the HLA-A2 molecule and an exogenously-added peptide is expressed on the cell surface only when the peptide has the capacity of binding to the HLA-A2 molecule. Panc-1 cells, that are HLA-A2 positive and express FOXM1, and PK-8 cells, that are HLA-A2 negative and FOXM1 positive, were used to evaluate the cytotoxic activity. As a result, killer T cells induced from two healthy individuals using the FOXM1 362-370, 373-382, and 640-649 peptides produced IFN-γ by recognizing the FOXM1 362-370, 373-382, and 640-649 peptides bound to HLA-A2 and expressed on T2-A2 cells. Furthermore, killer T cells from breast cancer patients that were induced using the above-mentioned peptides showed strong cytotoxic activity against panc-1 cells, but did not show cytotoxic activity against PK-8 cells. Thus, the induced killer T cells were found to show strong cytotoxic activity against cancer cell lines by specifically recognizing FOXM1 in an HLA-A2 restricted manner. From the above, it was revealed that the FOXM1 362-370, 373-382, and 640-649 peptides can induce FOXM1-specific human killer T cells in an HLA-A2 restricted manner, and such killer T cells can damage FOXM1-expressing cancer cells.

MODE FOR CARRYING OUT THE INVENTION

Unless otherwise defined, all technical and the scientific terms used herein have the same meaning as commonly understood by one of ordinary skill in the art to which the present invention belongs.

The peptides of the present invention are epitopes restricted to HLA-A2 which is an HLA allele frequently found in the Japanese and Caucasian populations. Using the binding affinity to HLA-A2 as an index, candidate HLA-A2 binding peptides derived from FOXM1 were selected. Killer T cells from two healthy individuals that were induced using the FOXM1 362-370, 373-382, and 640-649 peptides produced IFN-γ by recognizing the FOXM1 362-370 (YLVPIQFPV (SEQ ID NO: 1)), FOXM1-373-382 (SLVLQPSVKV (SEQ ID NO: 2)), and FOXM1-640-649 (GLMDLSTTPL (SEQ ID NO: 3)) peptides bound to HLA-A2 and expressed on T2-A2 cells. Killer T cells from breast cancer patients that were induced using the above-mentioned peptides showed strong cytotoxic activity against panc-1 cells, but did not show cytotoxic activity against PK-8 cells. Thus, the induced killer T cells were demonstrated to specifically recognize FOXM1 in an HLA-A restricted manner and show strong cytotoxic activity against cancer cell lines. Accordingly, it was revealed that the peptide of any one of FOXM1-362-370 (YLVPIQFPV (SEQ ID NO: 1)), FOXM1-373-382 (SLVLQPSVKV (SEQ ID NO: 2)), and FOXM1-640-649 (GLMDLSTTPL (SEQ ID NO: 3)) can induce FOXM1-specific human killer T cells in an HLA-A2 restricted manner, and such killer T cells can damage FOXM1-expressing cancer cells. FOXM1 was found to be highly expressed in almost all cases of lung cancer, bladder cancer, and pancreatic cancer, similarly to and in addition to intrahepatic bile duct cancer. Furthermore, FOXM1 was highly expressed in 40% or more of the cases in a wide variety of cancers such as cervical cancer, ovarian cancer, malignant lymphoma, breast cancer, stomach cancer, esophageal cancer, prostate cancer, hepatocellular carcinoma, colon cancer, and chronic myeloid leukemia. These facts show that FOXM1 is useful as a target for immunotherapy of various cancers.

(1) The peptides of the present invention, and agents for inducing anti-cancer immunity including thereof A peptide of the present invention is any one of (A) to (D) below:

(A) a peptide including the amino acid sequence of any one of SEQ ID NOs: 1 to 3;

(B) a peptide which includes the amino acid sequence of any one of SEQ ID NOs: 1 to 3, wherein one, two, or several amino acids are substituted, deleted, inserted, and/or added, and wherein the peptide shows cytotoxic (killer) T cell-inducing activity;

(C) the peptide of (B), in which the second amino acid from the N terminus is leucine or methionine; and (D) the peptide of (B), in which the C-terminal amino acid is valine or leucine.

Herein, "a peptide that shows cytotoxic (killer) T cell-inducing activity" means "a peptide having T cell-inducing activity that stimulates killer T cells (cytotoxic T cells/CTLs)".

The peptide of the present invention is a peptide (epitope peptide) having less than 40 amino acids, preferably less than 20 amino acids, more preferably less than about 15 amino acids, and including the amino acid sequence of any one of SEQ ID NOs: 1 to 3, and showing an activity of inducing killer T cells. Alternatively, the peptides of the present invention (epitope peptides) may include a peptide including the amino acid sequence of any one of SEQ ID NOs: 1 to 3, wherein one, two, or several amino acids are substituted, deleted, inserted, and/or added, as long as the ability to induce killer T cells is retained. The number of residues substituted, deleted, inserted, and/or added is generally five amino acids or less, preferably four amino acids or less, more preferably three amino acids or less, even more preferably one amino acid or two amino acids.

Variant peptides (i.e., peptides including amino acid sequences obtained by modifying the original amino acid sequences by substitution, deletion, insertion, and/or addition of one, two, or several amino acid residues) are known to retain the original biological activity (Mark D F et al., (1984) Proc Natl Acad Sci USA 81:5662-6; Zoller M J and Smith M, (1982) Nucleic Acids Res 10:6487-500; Dalbadie-McFarland G et al. (1982) Proc Natl Acad Sci USA 79:6409-13). The amino acid modification preferably retains the properties of the original amino acid side chains. Examples of the properties of amino acid side chains are shown below: hydrophobic amino acid side chains (A, I, L, M, F, P, W, Y, V); hydrophilic amino acid side chains (R, D, N, C, E, Q, G, H, K, S, T); and side chains having the following functional groups or characteristics in common: aliphatic side chains (G A, V, L, I, P); hydroxy group-containing side chains (S, T, Y); sulfur atom-containing side chains (C, M); carboxylic acid- and amide-containing side chains (D, N, E, Q); base-containing side chains (R, K, H); and aromatic ring-containing side chains (H, F, Y, W). The characters in the parentheses show one letter codes of amino acids.

In a preferred embodiment, the peptides of the present invention (immunogenic peptides) are nonapeptides (9-mer) or decapeptides (10-mer).

In order to obtain peptides with high binding affinity and killer T cell-inducing activity, the amino acid sequence of a partial peptide of naturally-occurring FOXM1 may be modified by substitution, deletion, insertion, and/or addition of one, two, or several amino acids. Herein, the term "several" refers to five or less, preferably three or less, more preferably two or less. Furthermore, since the regularity of the peptide sequences that have high affinity to HLA antigens is known (Kubo R T, et al., (1994) J. Immunol., 152, 3913-24; Rammensee H Q et al., (1995) Immunogenetics. 41:178-228; Kondo A, et al. (1995) J. Immunol. 155:4307-12), the peptides of the present invention (epitope peptides) can be modified based on the regularity in order to enhance their affinity to HLA antigens. For example, peptides with high HLA-A2 binding affinity can be obtained by substituting the second amino acid from the N terminus with leucine or methionine. Similarly, peptides with high HLA-A2 binding affinity can also be obtained by substituting the C-terminal amino acid with valine or leucine.

When the sequence of an epitope peptide is identical to a portion of the amino acid sequence of an endogenous or exogenous protein having a different function, side effects such as autoimmune disorders or allergy symptoms against a specific substance can be caused. In order to avoid such side effects, a modified epitope peptide should not be identical to the amino acid sequences of known proteins. For this purpose, it is necessary to carry out homology search using available databases to confirm that there is no endogenous or exogenous protein with a different function that shows 100% homology with the modified epitope peptide. By this procedure, risks caused by the above-mentioned amino acid sequence modification for increasing the binding affinity to HLA antigens and/or for increasing the killer T cell-inducing activity, can be avoided.

Although the above-mentioned peptides having high binding affinity to HLA antigens are expected to be highly effective as cancer vaccines, candidate peptides selected using high binding affinity as an index need to be examined whether they actually have killer T cell-inducing activity. The killer T cell-inducing activity can be confirmed by: inducing antigen-presenting cells having the human MHC antigen (for example, B lymphocytes, macrophages, and dendritic cells), and more specifically, inducing dendritic cells derived from human peripheral blood mononuclear leukocytes; stimulating them with a peptide of interest; then mixing them with CD8 positive cells; and measuring the cytotoxic activity towards target cells. As a reaction system, transgenic animals that express the human HLA antigen (as described in, for example, BenMohamed L, et al. (2000) Hum. Immunol. 61(8):764-79, Related Articles, Books, and Linkout) can be used. For example, target cells can be radiolabeled with $^{51}$Cr or such, and the cytotoxic activity can be calculated from the radioactivity released from the target cells. Alternatively, the target cells can be examined by: measuring IFN-γ produced and released by killer T cells in the presence of the antigen-presenting cells having an immobilized peptide; and visualizing the IFN-γ production zone in the culture medium using an anti-IFN-γ monoclonal antibody.

As shown in the Examples, the result of examining the killer T cell-inducing activity of peptides showed that peptides having high binding affinity to the HLA antigen do not necessarily have high inducing activity. However, the non-apeptides containing the amino acid sequence of any one of FOXM1-362-370 (YLVPIQFPV (SEQ ID NO: 1)), FOXM1-373-382 (SLVLQPSVKV (SEQ ID NO: 2)), and FOXM1 640-649 (GLMDLSTTPL (SEQ ID NO: 3)) showed particularly high killer T cell-inducing activity.

As described above, the present invention provides peptides showing killer T cell-inducing activity, more specifically, peptides including the amino acid sequence of any one of SEQ ID NOs: 1 to 3, and variants thereof (i.e., amino acid sequences in which one, two, or several amino acids are substituted, deleted, inserted and/or added). Preferably, the amino acid sequences of the peptides including the nine amino acids of any one of SEQ ID NOs: 1 to 3, or variants thereof are not identical to those of other endogenous proteins. Especially, peptides with high HLA-A2 binding affinity can be obtained by substituting the second amino acid from the N terminus with leucine or methionine, and/or by substituting the C-terminal amino acid with valine or leucine.

The peptides of the present invention may include modifications such as glycosylation, side chain oxidization, and phosphorylation, unless the peptides lose their killer T cell-inducing activity. Other modifications include, for example, D-amino acids and other amino acid analogues that can be used to increase the serum half-life of the peptides.

Methods for obtaining and producing the peptides of the present invention are not particularly limited. They may be chemically synthesized peptides or recombinant peptides produced by gene recombination techniques.

Chemically synthesized peptides of the present invention can be synthesized according to chemical synthesis methods such as the Fmoc method (fluorenylmethyloxycarbonyl method) and the t-Boc method (t-butyloxycarbonyl method). The peptides of the present invention can also be synthesized utilizing various commercially-available peptide synthesizers.

The peptides of the present invention can be produced as recombinant proteins by obtaining DNAs having the nucleotide sequences encoding the peptides, or variants or homologs thereof, and introducing them into a suitable expression system.

Expression vectors used may be preferably any vectors that can be autonomously duplicated in host cells, or can be incorporated into the chromosome of host cells, and contain a promoter at a suitable position to allow expression of a peptide-encoding gene. Transformants having a gene encoding the peptide of the present invention can be produced by introducing the above-mentioned expression vector into a host. The host may be any of bacteria, yeast, animal cells, and insect cells, and the expression vector may be introduced into the host using known techniques depending on the host.

In the present invention, the recombinant peptides can be isolated by culturing a transformant prepared as described above, producing and accumulating the peptides in the culture, and collecting the peptides of the present invention from the culture.

When the transformant is a prokaryote such as *E. coli* or an eukaryote such as yeast, the culture medium for these microorganisms may be either natural or synthetic medium, as long as it contains carbon source, nitrogen source, minerals, and such that can be utilized by the microorganisms, and allows efficient culture of the transformant. The culture conditions may be those conventionally used for culturing the microorganisms. After culturing, the peptides of the present invention can be isolated and purified from the culture of the transformant using conventional methods for peptide isolation and purification.

Peptides including an amino acid sequence in which one, two, or several amino acids are substituted, deleted, inserted, or added in the amino acid sequence of any one of SEQ ID NOs: 1 to 3 can be appropriately produced or obtained by a person skilled in the art based on the information on the DNA nucleotide sequence encoding the amino acid sequence of any one of SEQ ID NOs: 1 to 3. Specifically, a gene that encodes a peptide including an amino acid sequence in which one, two, or several amino acids are substituted, deleted, inserted and/or added in the amino acid sequence of any one of SEQ ID NOs: 1 to 3, and showing killer T cell-inducing activity can be produced by any methods known to persons skilled in the art, such as chemical synthesis, genetic engineering techniques, and mutagenesis. For example, the site-directed mutagenesis method, which is one of the genetic engineering techniques, is useful since it can introduce a specific mutation into a specific position. It can be carried out according to the methods described in Molecular Cloning: A laboratory Manual, $2^{nd}$ Ed., Cold Spring Harbor Laboratory, Cold Spring Harbor, N.Y., 1989 (hereinafter referred to as Molecular Cloning, $2^{nd}$ Ed.) and Current Protocols in Molecular Biology, Supplement 1-38, John Wiley & Sons (1987-1997) (hereinafter referred to as Current Protocols in Molecular Biology), etc.

The above-described peptides of the present invention can induce immunity against cancer, as shown below in the Examples. Therefore, the present invention provides agents for inducing immunity against cancer including one or more of the peptides of the present invention as an active ingredient.

The immunity-inducing agents of the present invention can be prepared as a mixed formulation combining two or more epitope peptides. Immunity-inducing agents formulated by combining multiple types of peptides may be a cocktail, or may be mutually bound using standard techniques. The epitope peptides to be combined may be peptides having different amino acid sequences derived from the same gene, or may be peptides having amino acid sequences derived from different genes. When the peptides of the present invention are administered, the administered peptides are presented on HLA antigens of antigen-presenting cells at a high density, and subsequently, killer T cells that react specifically to the complexes formed between the administered peptides and the HLA antigens are induced. Alternatively, by contacting dendritic cells collected from a subject with the peptides of the present invention (or by pulsing dendritic cells collected from a subject with the peptides of the present invention), antigen-presenting cells that present the peptides of the present invention on their cell surface can be obtained. By administrating these antigen-presenting cells back to the subject, killer T cells can be induced in the subject's body, and as a result, immune response to target cells presenting the peptides of the present invention can be enhanced.

When used in vitro or in vivo, preferably in vitro, the agents for inducing immunity against cancer of the present invention can induce helper T cells, killer T cells, or immunocyte populations including these cells, thereby providing immunity against cancer.

(2) Agents for treatment and/or prevention of cancer of the present invention (cancer vaccines)

It was shown in the Examples that the peptides of the present invention can induce cancer cell-specific killer T cells in vivo. On the other hand, it was shown in the previous invention that FOXM1 was highly expressed in most cases of lung cancer, cholangiocellular carcinoma, bladder cancer, renal cell carcinoma, prostate cancer, chronic myelogenous leukemia, malignant lymphoma, cervical cancer, osteosarcoma, breast cancer, soft tissue sarcoma, colon cancer, and such. Accordingly, the immunity-inducing agents including one or more of the peptides of the present invention as an active ingredient are expected to be effective as agents for treatment and/or prevention of cancer. That is, induction and activation of tumor-attacking killer T cells can be expected by injecting the peptides of the present invention together with a suitable adjuvant into the body, or by pulsing antigen-presenting cells such as dendritic cells with the peptides, and then injecting them into the body. Thus, as a result, anticancer effects can be expected. Furthermore, a gene encoding a peptide of the present invention can be incorporated into a suitable vector. Human antigen-presenting cells (dendritic cells, etc.) and bacteria such as BCG Mycobacterium tuberculosis that are transformed with the recombinant DNA, or viruses such as vaccinia viruses that have a DNA encoding the peptide of the present invention incorporated into their genome, can be used effectively as live vaccines for treatment and/or prevention of human cancer. The dosages and the administration methods for the cancer vaccines are the same as those for conventional smallpox vaccines and BCG vaccines.

In the present invention, the term "vaccine" (also called "immunogenic composition") refers to a substance that induces antitumor immunity or suppresses various cancers when inoculated to an animal. In the present invention, it was suggested that the peptide including the amino acid sequence of any one of SEQ ID NOs: 1 to 3 is an HLA-A2 restricted epitope peptide that can induce strong and specific immune response against FOXM1-presenting cells. Accordingly, the present invention also includes methods for inducing antitumor immunity by using the peptides including the amino acid sequence of any one of SEQ ID NOs: 1 to 3, or variants thereof that include substitution, deletion, insertion and/or addition of one, two, or several amino acids. In general, the antitumor immunity includes the following immune responses:

(1) induction of killer T cells against tumors containing FOXM1-expressing cells,
(2) induction of antibodies that recognize tumors containing FOXM1-expressing cells, and
(3) induction of antitumor cytokine production.

When a particular peptide induces any one of these immune responses through inoculation to an animal, the peptide is determined to have antitumor immunity-inducing effect. Induction of antitumor immunity by the peptide can be detected by observing in vivo or in vitro response of the immune system in a host to the peptide.

For example, methods for detecting induction of killer T cells are well known. A foreign substance that invades a living body is presented to T cells and B cells by the action of antigen-presenting cells (APCs). T cells that respond to antigens presented by antigen-presenting cells in an antigen-specific manner differentiate into killer T cells (also called cytotoxic T cells or CTLs) through stimulation by antigens, and then proliferate. Herein, this process is called "activation" of T cells. Induction of killer T cells by a specific peptide can be evaluated by presenting the peptide to T cells using peptide-pulsed antigen-presenting cells, and then detecting the induction of killer T cells. Furthermore, antigen-presenting cells have an effect of activating $CD4^+$ T cells, $CD8^+$ T cells, macrophages, eosinophils, and NK cells. Since $CD4^+$ T cells are important in antitumor immunity, the antitumor immunity-inducing action of the peptide can be evaluated using the effect on activating these cells as an index.

A method for evaluating the effect of inducing killer T cells that are induced using dendritic cells (DCs) as antigen-presenting cells is well known in the art. Among antigen-presenting cells, DCs have the strongest killer T cell-inducing effect. In this method, first, a test peptide is contacted with DCs, and then the DCs are contacted with T cells. T cells that have cytotoxic effect on target cells are detected from the T cells contacted with DCs. If the T cells show cytotoxic activity against the target cells, it means that the test peptide has the activity to induce cytotoxic T cells. The activity of killer T cells against target cells such as tumors can be detected, for example, using lysis of $^{51}Cr$-labeled tumor cells as an index. Alternatively, the degree of tumor cell damage can be evaluated using $^3H$-thymidine uptake activity or LDH (lactose dehydrogenase) release as an index.

Test peptides confirmed by these methods to show killer T cell-inducing activity are peptides that show DC-activating effect and subsequent killer T cell-inducing activity. Therefore, the peptides that show an activity of inducing killer T cells against tumor cells are useful as vaccines against cancers presenting FOXM1. Furthermore, antigen-presenting cells that have acquired the ability (activity) to induce killer T cells against cancers through contact with the peptides are useful as vaccines against cancers. Furthermore, killer T cells that have acquired cytotoxicity as a result of presentation of the peptides by antigen-presenting cells can also be used as vaccines against cancers presenting FOXM1. Methods of cancer treatment using antitumor immunity by antigen-presenting cells and killer T cells are called cytoimmunotherapy.

In general, when using peptides for cytoimmunotherapy, the efficiency of inducing killer T cells can be enhanced by combining multiple peptides having different structures. Therefore, when stimulating DCs with protein fragments, it is advantageous to use a mixture of multiple types of peptide fragments.

Induction of antitumor immunity by peptides can also be evaluated by observing the induction of antibody production against tumors. For example, when antibodies are induced against peptides by immunizing laboratory animals with the peptides, and they suppress growth, proliferation, and/or metastasis of tumor cells, it is determined that the peptides induce antitumor immunity.

Antitumor immunity can be induced by administering a vaccine of the present invention, and the induction of antitumor immunity enables treatment and/or prevention of cancers. Effects of cancer treatment and/or prevention of cancer development may include inhibition of cancer cell growth, regression of cancer cells, and suppression of cancer cell development. Decrease in the mortality rate of individuals with cancer, decrease in tumor markers in blood, and reduction of detectable symptoms associated with cancer are also included in the effects of treatment and/or prevention of cancer. The therapeutic and/or preventive effects of a vaccine against cancer are preferably statistically significant compared to those of a control without vaccine administration. For example, the effects are preferably observed at a significance level of 5% or less. Statistical methods such as Student t-test, Mann-Whitney U test, ANOVA, or such may be used for determining the statistical significance.

In the present invention, the subject is preferably a mammal Examples of mammals include humans, non-human primates, mice, rats, dogs, cats, horses, and cattle, but are not limited hereto.

The peptides of the present invention can be administered to a subject in vivo or ex vivo. Furthermore, to produce an immunogenic composition for treatment and/or prevention of cancer, the immunogenic peptides of the present invention, that is, nonapeptides selected from the amino acid sequences of SEQ ID NOs: 1 to 3, and mutant peptides thereof, may be used.

More specifically, the present invention provides pharmaceutical agents for treatment of tumor or prevention of tumor growth, metastasis, and such, which include one or more of the peptides of the present invention as an active ingredient. The peptides of the present invention are particularly useful for treatment of tumors such as pancreatic cancer, cholangiocellular carcinoma, stomach cancer, colon cancer, non-small-cell lung cancer, testicular cancer, cervical cancer, osteosarcoma, and soft tissue sarcoma.

The peptides of the present invention can be administered directly to a subject as pharmaceutical agents formulated by conventional formulation methods. Such formulations may contain, in addition to the peptides of the present invention, pharmaceutically acceptable carriers, excipients, and such, as necessary. The pharmaceutical agents of the present invention may be used for treatment and/or prevention of various tumors.

Furthermore, to effectively establish cellular immunity, adjuvants can be mixed into pharmaceutical agents for treatment and/or prevention of tumors including one or more of the peptides of the present invention as an active ingredient. The agents may be co-administered with other active ingredients such as antitumor agents. Appropriate formulations also include granules. Appropriate adjuvants are described in the literature (Johnson A G. (1994) Clin. Microbiol. Rev., 7:277-89). Examples of adjuvants include Freund's incomplete adjuvant, BCG, trehalose dimycolate (TDM), lipopolysaccharide (LPS), aluminum potassium sulfate adjuvant, silica adjuvant, aluminum phosphate, aluminum hydroxide, and alum, but are not limited thereto. Furthermore, liposomal formulations, granular formulations in which a drug is bound to beads having a diameter of several micrometers, and formulations in which lipids are bonded to the aforementioned peptides may be conveniently used. Administration methods may be oral administration, intradermal injection, subcutaneous injection, intravenous injection, or such, and may include systemic administration and local administration near the target tumor.

The dose of the peptides of the present invention can be adjusted appropriately depending on the disease to be treated, age and body weight of the patient, administration method, and such. The dose is usually 0.001 mg to 1000 mg, preferably 0.01 mg to 100 mg, and more preferably 0.1 mg to 10 mg. Preferably, administration is performed once a few days to a few months, but those skilled in the art can easily select the appropriate dose and administration method; and selection and optimization of these parameters are fully within the scope of conventional techniques. The form of formulations is not particularly limited, and they may be freeze-dried, or granulated by adding excipients such as sugar.

Auxiliary agents that can be added to the pharmaceutical agents of the present invention for increasing the killer T cell-inducing activity include bacterial components of BCG bacteria and such including muramyl dipeptide (MDP), ISCOM described in Nature, vol. 344, p873 (1990), QS-21 of saponin series described in J. Immunol. vol. 148, p1438 (1992), liposome, and aluminum hydroxide. Furthermore, immunostimulants such as lentinan, sizofiran, and picibanil can also be used as auxiliary agents. Cytokines and such that enhance the growth and differentiation of T cells, such as IL-2, IL-4, IL-12, IL-1, IL-6, and TNF, as well as α-galactosylceramide which activates NKT cells, and CpG and lipopolysaccharides (LPS) which activate the natural immune system by binding to Toll-like receptors, and such, can also be used as auxiliary agents.

Vaccine compositions of the present invention contain a component that primes killer T cells. Lipids have been identified as a substance for priming against viral antigens in vivo. For example, palmitic acid residues can be bound to the ε-amino group and α-amino group of a lysine residue, and then linked to an immunogenic peptide of the present invention. The lipidated peptides can be directly administered by incorporating them into a micelle or particle, or encapsulating them into a liposome, or emulsifying them in an adjuvant. Another example of lipid priming is priming with an *E. coli* lipoprotein such as tripalmitoyl-S-glycerylcysteinyl-serylserine (P3CSS) when covalently bound to a suitable peptide (Deres K., et al., (1989) Nature 342:561-4).

The immunogenic peptides of the present invention can be expressed by viral vectors or bacterial vectors. Examples of appropriate expression vectors include avirulent viral hosts such as vaccinia and fowlpox. For example, a vaccinia virus can be used as a vector to express a nucleotide sequence encoding the peptide. By introducing the recombinant vaccinia virus into host cells, the immunogenic peptides are expressed, eliciting immune response. The immunization method using vaccinia vectors is described, for example, in U.S. Pat. No. 4,722,848. Bacille Calmette-Guerin (BCG) may also be used. BCG vectors are described in Stover C K, et al., (1991) Nature 31:456-60. A wide variety of other vectors useful for therapeutic administration or immunization, including adenovirus vectors and adeno-associated virus vectors, retroviral vectors, typhoid *bacillus* (*Salmonella typhi*) vectors, and detoxified anthrax toxin vectors, are known in the art. See, for example, Shata M T, et al., (2000) Mol. Med. Today 6:66-71; Shedlock D J and Weiner D B., et al., (2000) J. Leukoc. Biol. 68:793-806; and Hipp J D, et al., (2000) In Vivo 14:571-85.

Killer T cells can be effectively induced in the body of a patient by adding an antigenic peptide in vitro to cells collected from the patient or cells from another individual sharing some of the HLA alleles (allogeneic cells), and presenting the antigen, and then administering the cells to the patient intravascularly, locally to the tumor, or such. Alternatively, after in vitro induction of killer T cells by adding the peptide to the patient's peripheral blood lymphocytes and culturing them in vitro, the cells can be administered to the patient intravascularly, locally to the tumor, or such. Such cell transfer treatment has already been carried out as cancer therapy, and is a well-known method among those skilled in the art.

The type of cancers in the present invention is not particularly limited, and specific examples include esophageal cancer, breast cancer, thyroid cancer, colon cancer, pancreatic cancer, malignant melanoma (melanoma), malignant lymphoma, osteosarcoma, pheochromocytoma, head and neck cancer, uterine cancer, ovarian cancer, brain tumor, chronic myelogenous leukemia, acute myelogenous leukemia, renal cancer, prostate cancer, lung cancer, stomach cancer, liver cancer, gallbladder cancer, testicular cancer, thyroid cancer, bladder cancer, sarcoma, etc. Examples of cancers for which application of the present invention is suitable include biliary tract cancer, lung cancer, pancreatic cancer, and bladder cancer.

(3) Antibodies of the Present Invention

The present invention also relates to antibodies that recognize a portion of or the entire peptide of the present invention mentioned above as an epitope (antigen), and relates to killer T cells that are induced by in vitro stimulation using the proteins or peptides. In general, the killer T cells demonstrate more potent antitumor activity than the antibodies.

Furthermore, similarly to the peptides of the present invention, the antibodies of the present invention are useful as prophylactic and/or therapeutic agents against cancers expressing FOXM1, as long as they can inhibit the activity of the FOXM1 cancer antigen. In a practical use, the peptides or antibodies of the present invention may be administered as they are, or by injection with a pharmaceutically acceptable carrier and/or diluent, together with an adjuvant as necessary. Alternatively, they can be administered by transdermal absorption through mucous membranes by the spray method or such. More specifically, herein, human serum albumin is an example of carriers; and PBS, distilled water, and such are examples of diluents.

The antibodies of the present invention may be polyclonal antibodies or monoclonal antibodies, and can be produced by methods known to those skilled in the art.

For example, polyclonal antibodies can be obtained by immunizing mammals or avian species with a peptide of the present invention as an antigen, and collecting blood from the mammals or avian species, and separating and purifying antibodies from the collected blood. For example, mammals such as mouse, hamster, guinea pig, chicken, rat, rabbit, dog, goat, sheep, and bovine, or avian species can be immunized. Methods of immunization are known to those skilled in the art, and the antigen can be administered, for example, two or three times at an interval of, for example, 7 to 30 days. The dosage can be, for example, approximately 0.05 mg to 2 mg of antigen per administration. The route of administration is not particularly limited, and can be suitably selected from subcutaneous administration, intradermal administration, intraperitoneal administration, intravenous administration, intramuscular administration, and such. Furthermore, the antigen can be applied after dissolving it in a suitable buffer, for example, a buffer containing a conventional adjuvant such as Freund's complete adjuvant and aluminum hydroxide.

After the immunized mammals or avian species are reared for a certain period of time, when the antibody titer has increased, they can be additionally immunized with, for example, 100 µg to 1000 µg of the antigen. Blood can be collected from the immunized mammals or avian species one to two months after the final administration, and the blood can be separated and purified by conventional methods such as centrifugation, precipitation using ammonium sulfate or polyethylene glycol, chromatography such as gel filtration chromatography, ion exchange chromatography, affinity chromatography, and such, to obtain the polyclonal antibodies that recognize the peptides of the present invention as a polyclonal antiserum.

On the other hand, monoclonal antibodies can be obtained by preparing hybridomas. For example, hybridomas can be obtained by cell fusion of antibody-producing cells with myeloma cell lines. Hybridomas that produce monoclonal antibodies of the present invention can be obtained by cell fusion methods such as those indicated below.

Spleen cells, lymph node cells, B lymphocytes, and such from immunized animals are used as antibody-producing cells. The peptides of the present invention are used as antigens. Animals such as mouse and rat can be used as immunized animals, and administration of antigens to these animals is carried out by conventional methods. For example, animals are immunized by administering a suspension or emulsion of a peptide of the present invention, which is an antigen, with an adjuvant such as Freund's complete adjuvant and Freund's incomplete adjuvant, to the animals several times intravenously, subcutaneously, intradermally, intraperitoneally, or such. Antibody-producing cells such as spleen cells are obtained from the immunized animals, and can be fused with myeloma cells by known methods (G. Kohler et al., Nature, 256, 495 (1975)) to generate hybridomas.

For mice, examples of myeloma cell lines used for cell fusion include, for example, the P3X63Ag8, P3U1, Sp2/0 lines, etc. A fusion-promoting agent such as polyethylene glycol and Sendai virus is used for cell fusion, and hypoxanthine/aminopterin/thymidine (HAT) medium is used for selecting hybridomas by a conventional method after cell fusion. Hybridomas obtained by cell fusion are cloned by the limiting dilution method or such. As necessary, cell lines producing monoclonal antibodies that specifically recognize the peptides of the present invention can be obtained by using the peptides of the present invention in screening with an enzyme immunoassay method.

In addition to the above-mentioned methods, immunized cells can be modulated by stimulating human lymphocytes such as EB virus-infected lymphocytes in vitro using the peptides of the present invention, cells expressing the peptides, or lysates thereof. Human antibodies that bind to the peptides of the present invention can be obtained by fusing the immunized lymphocytes with human-derived bone marrow cells such as U266 (Japanese Patent Application Kokai Publication No. (JP-A) S63-17688 (unexamined, published Japanese patent application)).

In order to produce monoclonal antibodies of interest from hybridomas thus obtained, the hybridomas can be cultured by conventional culture methods or ascites-forming methods, and the monoclonal antibodies can be purified from the culture supernatant or ascites. Purification of monoclonal antibodies from culture supernatants or ascites can be performed by conventional methods. For example, ammonium sulfate fractionation, gel filtration, ion exchange chromatography, affinity chromatography, and such can be suitably combined and used.

Transgenic animals that have a group of human antibody genes can be immunized using the peptides of the present invention, cells expressing the peptides, or lysates thereof. Antibody-producing cells can be collected from the immunized transgenic animals, and fused with the above-described myeloma cell lines to obtain hybridomas. Monoclonal antibodies of interest can then be produced from the hybridomas (WO92/03918; WO94/02602; WO94/25585; WO94/33735; WO96/34096).

Furthermore, antibody-producing immune cells such as immunized lymphocytes can be immortalized using oncogenes, and used for preparation of monoclonal antibodies.

Monoclonal antibodies thus obtained can also be modulated using gene manipulation techniques (Borrbaeck and Larrick, (1990) Therapeutic Monoclonal Antibodies). For example, recombinant antibodies can be prepared by cloning a DNA encoding an antibody from antibody-producing cells such as hybridomas and immunized lymphocytes, and inserting it into a suitable vector, and introducing this into host cells.

The antibodies of the present invention may be antibody fragments or modified antibodies, as long as they bind to the peptides of the present invention. The antibody fragments can be Fab, F(ab')$_2$, Fv, or a single chain Fv (scFv) in which Fv fragments derived from H and L chains are linked together with a suitable linker (Huston et al., (1998) Proc Natl Acad Sci USA 85: 5879-83). More specifically, the antibody fragments can be prepared by treating antibodies with an enzyme such as papain and pepsin (Co et al., (1994) J Immunol 152:2968-76; Better and Horwitz, (1989) Methods Enzymol 178: 476-96; Pluckthun and Skerra, (1989) Methods Emzymol 178:497-515; Lamoyi (1986) Methods Enzymol 121:

652-63; Rousseaux et al., (1986) Methods Enzymol 121:663-9; Bird and Walker, (1991) Trends Biotech 9:132-7).

The antibodies of the present invention include modified antibodies obtained by binding antibodies to various molecules such as polyethylene glycol (PEG). The antibodies can be modified by conventional chemical modification methods known in the art.

The antibodies of the present invention include chimeric antibodies including a variable region derived from a non-human antibody and a constant region derived from a human antibody, and humanized antibodies including a complementarity determining region (CDR) derived from a non-human antibody, a framework region (FR) derived from a human antibody, and a constant region derived from a human antibody. Such antibodies can be prepared by conventional methods known in the art. Humanized antibodies are obtained by substituting the CDR sequence region of a human antibody with a rodent CDR region having desired binding activity (Verhoeyen et al., (1988) Science 239:1534-6). Accordingly, compared to chimeric antibodies, humanized antibodies are antibodies in which a smaller region of a human antibody is substituted with a corresponding region of non-human origin.

A complete human antibody having a human variable region in addition to human framework and constant regions can also be produced. For example, in an in vitro method, screening can be carried out using a recombinant library of bacteriophages on which human antibody fragments are displayed (Hoogenboom and Winter, (1992) J Mol Biol 227: 381-8). Similarly, human antibodies can be produced by introducing human immunoglobulin loci into transgenic animals whose endogenous immunoglobulin genes have been partially or completely inactivated (U.S. Pat. Nos. 6,150,584, 5,545,807, 5,545,806, 5,569,825, 5,625,126, 5,633,425, and 5,661,016).

The antibodies obtained as stated above can be purified to homogeneity by conventional methods in the art. For example, common methods of protein separation and purification can be used. The antibodies can be separated and purified by a combination of column chromatography such as affinity chromatography, filtration, ultrafiltration, salting out, dialysis, SDS polyacrylamide gel electrophoresis, isoelectric focusing, and such; however, separation and purification methods are not limited thereto (Antibodies: A Laboratory Manual, Ed Harlow and David Lane, (1988) Cold Spring Harbor Laboratory). Protein A columns and protein G columns can be used for affinity columns. Examples of protein A columns include HyperD, POROS, and Sepharose F. F (Pharmacia).

Examples of chromatography other than affinity chromatography include ion exchange chromatography, hydrophobic chromatography, gel filtration, reverse-phase chromatography, adsorption chromatography, and such (Strategies for Protein Purification and Characterization: A Laboratory Course Manual. Ed Daniel R. et al.). Liquid chromatography such as HPLC and FPLC can also be used for chromatography.

The antigen-binding affinity of the antibodies of the present invention may be measured using, for example, absorbance measurement, enzyme-linked immunosorbent assay (ELISA), enzyme immunoassay (ETA), radioimmunoassay (RIA), and immunofluorescence assay; however, the methods are not limited thereto. For ELISA, the antibodies of the present invention are immobilized onto a plate, and the peptides of the present invention are added, then a sample containing a culture supernatant of antibody-producing cells or purified antibodies is added. Subsequently, a labeled secondary antibody that can recognize and detect the antibody whose antigen-binding affinity is to be measured, is added. After washing the plate, reagents for detecting the label of the secondary antibody are added and the absorbance or such is measured. For example, enzymes such as alkaline phosphatase can be used as a label for the secondary antibody, and enzyme substrates such as p-nitrophenyl phosphate can be used as a reagent for detection. BIAcore (Pharmacia) can also be used to evaluate the activity of the antibodies.

The antibodies of the present invention can detect the peptides of the present invention contained in samples. Specifically, the presence of the peptides of the present invention in cancer tissues can be confirmed, for example, by contacting cancer tissue biopsies with the antibodies of the present invention.

Prior to using the peptides of the present invention in therapeutic and/or prophylactic treatment of cancer, it is possible to predict whether the effect is promising in a test subject before initiation of the treatment by evaluating the expression of the peptides of the present invention in the cancer to be treated using the antibodies of the present invention.

Furthermore, since the antibodies of the present invention recognize FOXM1 peptide fragments whose expression is augmented in various cancer cells, their application is expected to be applicable not only in diagnosis but also for treatment.

(4) Helper T Cells, Killer T Cells, or Immunocyte Populations Including them

The present invention also relates to killer T cells and helper T cells induced by in vitro stimulation using the peptides of the present invention, as well as immunocyte populations including the killer T cells and helper T cells. For example, tumor responsive activated T cells are induced when peripheral blood lymphocytes or tumor-infiltrating lymphocytes are stimulated in vitro using the peptides of the present invention, and these activated T cells can be effectively used for adoptive immunotherapy in which the cells are administered to a cancer patient intravascularly, locally to the tumor, or such. Alternatively, dendritic cells which are potent antigen-presenting cells can be pulsed with the peptides of the present invention or genetically transformed to express the peptides, and anti-tumor immune response can be induced by stimulating T cells in vivo or in vitro using the dendritic cells.

Killer T cells, helper T cells, or immunocyte populations including them are preferably induced by in vivo or in vitro stimulation using the peptides of the present invention and adjuvants. Examples of adjuvants used herein include mineral oil, aluminum hydroxide, *Mycobacterium tuberculosis* formulations, hemolytic *streptococcus* formulations, Polyporaceae formulations, other adjuvants, cell growth factors, and cytokines.

Tumors can be suppressed and cancers can be prevented and/or treated by transfusion of the thus-obtained helper T cells, killer T cells, or immunocyte populations including them into a cancer patient intravascularly, locally to the tumor, or such.

Killer T cells, helper T cells, or immunocyte populations including them that are capable of suppressing tumors as described above can be produced using the peptides of the present invention. Therefore, the present invention provides cell culture media containing the peptides of the present invention. Killer T cells, helper T cells, or immunocyte populations including them capable of suppressing tumors can be prepared using the cell culture media. Furthermore, the present invention provides a cell culture kit including the above-mentioned cell culture medium and a cell culture vessel for production of killer T cells, helper T cells, or immunocyte populations including them.

(5) Antigen-Presenting Exosomes

The present invention further provides an endocytic vesicle called "exosome" which presents on its surface a complex formed with a peptide of the present invention and an HLA antigen. Exosomes can be prepared, for example, by the methods described in detail in the Japanese translations of Japanese Patent Application Kohyo Publication No. (JP-A) H11-510507 (unexamined Japanese national phase publication corresponding to a non-Japanese international publication) and JP-A (Kohyo) 2000-512161. Preferably, exosomes are prepared using antigen-presenting cells obtained from a subject of treatment and/or prevention. Exosomes of the present invention can be injected as a cancer vaccine in a similar manner as the peptides of the present invention.

The HLA antigenic type used in the present invention should match the HLA antigenic type of a subject in need of the treatment and/or prevention. For example, the HLA antigenic type is HLA-A2, and preferably, HLA-A2 (HLA-A*0201). "HLA-A2" signifies a protein, while "(HLA-A*0201)" signifies a gene corresponding to a segment of the protein, because of the lack of terminology for expressing segments of the protein at present.

(6) Methods for Inducing Antigen-Presenting Cells and Killer T Cells

The present invention provides methods for inducing antigen-presenting cells using one or more of the peptides of the present invention. Antigen-presenting cells can be induced by contacting dendritic cells induced from peripheral blood monocytes with one or more of the peptides of the present invention to stimulate the dendritic cells. When the peptides of the present invention are administered into a subject, antigen-presenting cells presenting the peptides of the present invention on their surface can be induced in the body of the subject. Alternatively, an ex vivo method can be used, in which antigen-presenting cells are contacted with the peptides of the present invention (or pulsing antigen-presenting cells with the peptides of the present invention), and then the cells are administered to a subject as a vaccine. For example, ex vivo administration may include the steps of:

(1) collecting antigen-presenting cells from a subject; and (2) contacting the antigen-presenting cells of step (1) with a peptide of the present invention (or pulsing the antigen-presenting cells of step (1) with a peptide of the present invention).

The antigen-presenting cells obtained in step (2) can be administered into a subject as a vaccine.

The present invention also provides methods for inducing antigen-presenting cells that show a killer T cell induction activity. The methods include the step of transfecting antigen-presenting cells in vitro with a gene including a polynucleotide encoding one or more of the peptides of the present invention. The gene to be transfected can be a DNA or RNA. For transfection, various methods conventionally performed in the art, such as lipofection, electroporation, and a calcium phosphate method can be suitably used, but the methods are not limited thereto. More specifically, transfection can be performed as described in Reeves M E, et al., (1996) Cancer Res., 56:5672-7; Butterfield L H, et al., (1998) J. Immunol., 161:5607-13; Boczkowski D, et al., (1996) J Exp. Med., 184:465-72; and the published Japanese translation of WO2000/509281. When the genes are transfected into antigen-presenting cells, they are transcribed and translated in the cells. The resulting proteins are subsequently processed via the MHC class I and class II pathways, and are presented on the surface of the antigen-presenting cells as partial peptides through the antigen-presenting pathway.

The present invention also provides methods for inducing killer T cells using one or more of the peptides of the present invention. By administering one or more of the peptides of the present invention to a subject, killer T cells can be induced in the body of the subject, thus augmenting the immune system that targets cancer cells presenting FOXM1 in tumor tissues. Alternatively, activated killer T cells can be induced by contacting antigen-presenting cells and CD8 positive cells from the subject with one or more of the peptides of the present invention in vitro, and by contacting peripheral-blood mononuclear leukocytes with the antigen-presenting cells in vitro to stimulate the cells. In ex vivo therapeutic methods, the immune system that targets cancer cells presenting FOXM1 in tumor tissues in a subject can be augmented by returning the activated killer T cells into the body of the subject. For example, the methods include the steps of:

(1) collecting antigen-presenting cells from a subject;

(2) contacting the antigen-presenting cells of step (1) with a peptide of the present invention (or pulsing the antigen-presenting cells of step (1) with a peptide of the present invention);

(3) mixing and co-culturing the antigen-presenting cells of step (2) with $CD8^+$ T cells to induce cytotoxic T cells; and (4) collecting $CD8^+$ T cells from the co-culture of step (3).

$CD8^+$ T cells having cytotoxic activity obtained in step (4) can be administered to a subject as a vaccine.

The present invention also provides isolated killer T cells induced using one or more of the peptides of the present invention. Preferably, killer T cells induced by the method of the present invention are derived from a subject who receives the treatment and/or prevention. The cells can be administered in combination with other agents containing antigen-presenting cells or exosomes presenting one or more of the peptides of the present invention. The obtained killer T cells are specific to target cells presenting the same peptide used for induction. The target cells are cells endogenously expressing FOXM1, or cells transfected with the FOXM1 gene. By stimulation with a peptide of the present invention, cells presenting the peptide of the present invention on their surface, such as cancer cells from pancreatic cancer, cholangiocellular carcinoma, stomach cancer, colon cancer, non-small-cell lung cancer, testicular cancer, cervical cancer, osteosarcoma, and soft tissue sarcoma, can be targets for attack.

The present invention also provides antigen-presenting cells presenting a complex formed with an HLA antigen and one or more of the peptides of the present invention. The antigen-presenting cells expressing one or more of the peptides of the present invention or nucleotides encoding such peptides are preferably collected from a subject who receives the treatment and/or prevention. The peptides of the present invention, antigen-presenting cells presenting the peptides, exosomes, or activated killer T cells can be administered as a vaccine in combination with other drugs.

The present invention will be further described with reference to the Examples below; however, it is not to be construed as being limited thereto.

All prior art references cited in the present specification are incorporated herein by reference.

EXAMPLES

Example 1

(1) Selection of FOXM1 Peptides that Show Affinity to HLA-A2

Amino acid sequences of human FOXM1 were analyzed using the BIMAS system, and 23 types that are predicted to have binding affinity to HLA-A2 of 20 or more were selected.

TABLE 1

| PEPTIDE POSITION | PEPTIDE AMINO ACID SEQUENCE | BINDING AFFINITY SCORE |
|---|---|---|
| FOXM1 42-50 | NQAEASKEV (SEQ ID NO: 4) | 29 |
| FOXM1 241-249 | YMAMIQFAI (SEQ ID NO: 5) | 201 |
| FOXM1 256-264 | RMTLKDIYT (SEQ ID NO: 6) | 30 |
| FOXM1 288-296 | NLSLHDMFV (SEQ ID NO: 7) | 383 |
| FOXM1 290-299 | SLHDMFVRET (SEQ ID NO: 8) | 53 |
| FOXM1 355-363 | LLPRVSSYL (SEQ ID NO: 9) | 200 |
| FOXM1 355-364 | LLPRVSSYLV (SEQ ID NO: 10) | 118 |
| <u>FOXM1 362-370</u> | YLVPIQFPV (SEQ ID NO: 1) | <u>1856</u> |
| FOXM1 366-375 | IQFPVNQSLV (SEQ ID NO: 11) | 44 |
| <u>FOXM1 373-382</u> | SLVLQPSVKV (SEQ ID NO: 2) | <u>70</u> |
| FOXM1 374-382 | LVLQPSVKV (SEQ ID NO: 12) | 38 |
| FOXM1 409-418 | LLAEEGIAPL (SEQ ID NO: 13) | 342 |
| FOXM1 429-438 | LLFGEGFSPL (SEQ ID NO: 14) | 255 |
| FOXM1 545-553 | LLFSEGPST (SEQ ID NO: 15) | 47 |
| FOXM1 571-579 | SQLSYSQEV (SEQ ID NO: 16) | 26 |
| FOXM1 616-625 | KVGGIDFSPV (SEQ ID NO: 17) | 40 |
| <u>FOXM1 640-649</u> | GLMDLSTTPL (SEQ ID NO: 3) | <u>324</u> |
| FOXM1 660-669 | RLLSSEPLDL (SEQ ID NO: 18) | 79 |
| FOXM1 661-669 | LLSSEPLDL (SEQ ID NO: 19) | 36 |
| FOXM1 702-711 | SLTEGLVLDT (SEQ ID NO: 20) | 70 |
| FOXM1 711-719 | TMNDSLSKI (SEQ ID NO: 21) | 71 |
| FOXM1 719-728 | ILLDISFPGL (SEQ ID NO: 22) | 1047 |
| FOXM1 720-728 | LLDISFPGL (SEQ ID NO: 23) | 28 |

The HLA-A2 restricted human killer T cell epitopes that were identified in the present invention are underlined.

Example 2

Induction of Human Killer T Cells by HLA-A2 Binding FOXM1 Peptides (1) Blood Collection Blood samples (50 ml) were collected with informed consent from healthy individuals and HLA-A2 positive breast cancer patients who were undergoing treatment at the Kumamoto University Medical School Hospital. Then, peripheral blood mononuclear cells were isolated using the Ficoll-Conray density gradient centrifugation method according to a previously reported method (Nakatsura, T. et al., Eur. J. Immunol. 32, 826-836, 2002).

(2) Separation of CD8 Positive Cells from Peripheral Blood Mononuclear Cells and Induction of Killer T Cells FOXM1 peptide-specific killer T cells were induced from the isolated peripheral blood mononuclear cells. Killer T cells were induced according to the report by Komori, H. et al. (Komori, H. et al., Clin. Cancer. Res. 12: 2689-2697, 2006). First, CD8 positive cells in the peripheral blood mononuclear cells were separated using MACS. CD8 negative cells were cultured for four days in the presence of GM-CSF (100 ng/mL) and IL-4 (20 ng/mL) for differentiation into dendritic cells. Thereafter, OK-432 (0.1 KE/mL) was added for maturation of the dendritic cells. On day seven, each FOXM1 peptide (10 µM) was added, and then the dendritic cells were co-cultured with the CD8 positive cells in the presence of IL-7 (10 ng/mL). After two days of co-culturing with the CD8 positive cells, IL-2 (20 IU/mL) was added. Antigenic stimulation with the dendritic cells derived from autologous CD8 negative cells was repeated three times at one week interval to induce peptide-specific killer T cells.

(3) Examination of the FOXM1-Specific Killer T-Cell Activity by ELISPOT Assay

Figure 1A:
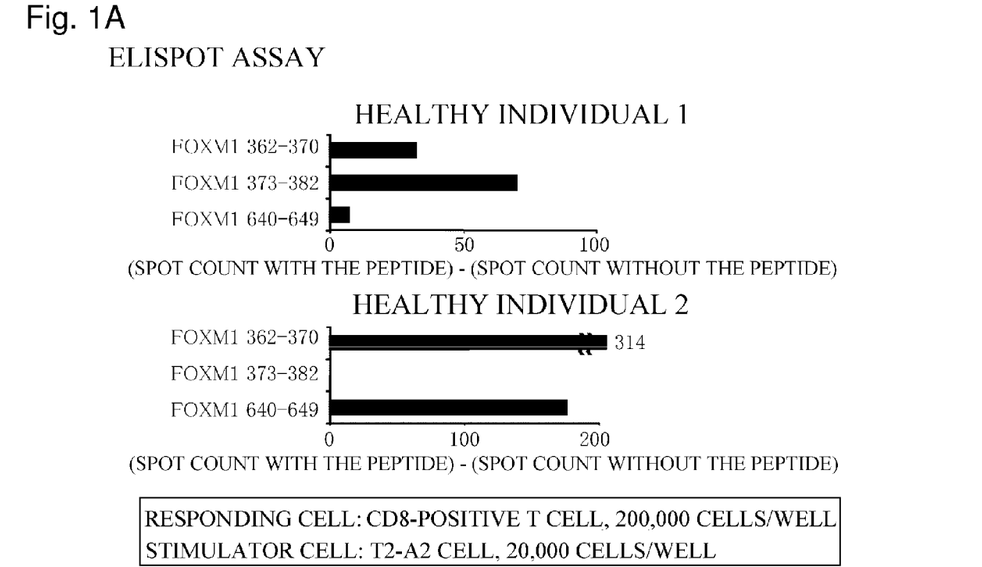
Figure 1B:
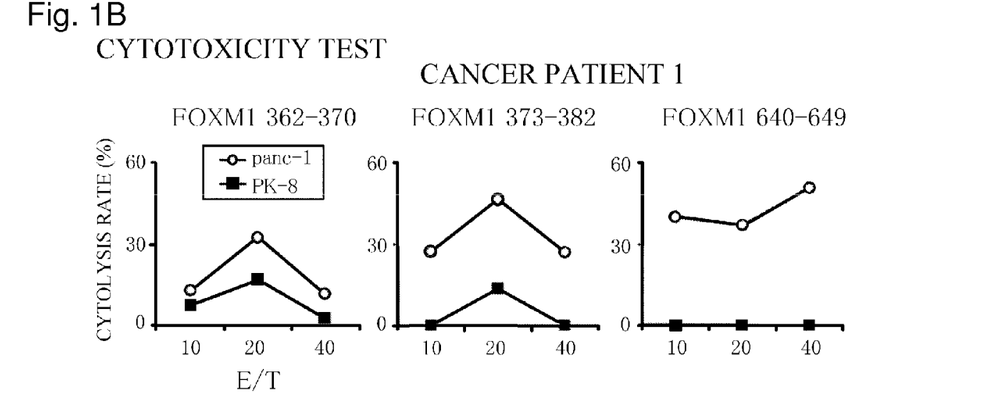

ELISPOT assay was used to examine whether or not killer T cells induced by the FOXM1 peptides produce IFN-γ by actually and specifically reacting to these FOXM1-derived peptides. ELISPOT assay was carried out by a previously reported method (Komori, H. et al., Clin. Cancer. Res. 12: 2689-2697, 2006). As a result, FOXM1 peptide-specific killer T cell activation was observed for the killer T cells induced with the FOXM1 362-370, 373-382, and 640-649 peptides (FIG. 1). FIG. 1 shows representative results of the analysis of FOXM1 peptide-induced killer T cells.

(4) Examination of the Cytotoxic Activity of Killer T Cells by Cytotoxicity Test The cytotoxic activity of the induced FOXM1 peptide-specific killer T cells was examined by a cytotoxicity test, using the HLA-A2 positive and FOXM1-expressing cell line panc-1 and the HLA-A2 negative and FOXM1-expressing pancreatic cancer cell line PK-8 as stimulator cells. The killer T cells were evaluated for cytotoxic activity using a cytotoxicity test by chromium release assay. The chromium release assay was performed using a previously reported method (Monji, M. et al., Clin. Cancer. Res. 10: 6047-6057, 2004). As a result, HLA-A2 restricted and FOXM1-specific cytotoxic activity was observed for the killer T cells induced with the FOXM1 362-370, 373-382, and 640-649 peptides (FIG. 1).

INDUSTRIAL APPLICABILITY

In the present invention, cancer peptide vaccines that can target approximately 30% of Japanese cancer patients with biliary tract cancer, lung cancer, pancreatic cancer, and such highly expressing FOXM1, were developed by identifying FOXM1 peptides that can bind to HLA-A2 and activate cancer cell-damaging killer T cells. If the effectiveness of the FOXM1 peptides presented to killer T cells by HLA-A2 can be demonstrated in translational medicine, the possibility of clinically applying to Caucasians may be improved. By identifying peptides presented to killer T cells by HLA-A2, which is positive in Caucasians at high frequency, the peptides can be applied not only to approximately 30% of Japanese patients with cancers that highly express FOXM1, but also to many Caucasian cancer patients.

The invention claimed is:

1. A method for treating cancer expressing FOXM1, which comprises the step of administering an isolated peptide of (A) or (B) below:

(A) a peptide of less than 15 amino acids comprising the amino acid sequence of SEQ ID NO: 2;

(B) a peptide of less than 15 amino acids which comprises the amino acid sequence of SEQ ID NO: 2, in which one or two amino acid(s) are substituted, wherein the peptide shows cytotoxic (killer) T cell-inducing activity.

2. The method of claim 1, wherein the peptide consists of the amino acid sequence of SEQ ID NO: 2.

* * * * *